United States Patent [19]

Kudsk

[11] Patent Number: 5,317,012

[45] Date of Patent: May 31, 1994

[54] HUMAN GROWTH HORMONE INDUCED IMPROVEMENT IN DEPRESSED T4/T8 RATIO

[75] Inventor: Kenneth A. Kudsk, Memphis, Tenn.

[73] Assignee: The University of Tennessee Research Corporation, Knoxville, Tenn.

[21] Appl. No.: 12,783

[22] Filed: Jan. 29, 1993

Related U.S. Application Data

[63] Continuation of Ser. No. 770,919, Oct. 4, 1991, abandoned.

[51] Int. Cl.$^5$ ............................................. A61K 37/36
[52] U.S. Cl. ......................................... 514/12; 514/21
[58] Field of Search .................................. 514/12, 21

[56] References Cited

U.S. PATENT DOCUMENTS

| | | | |
|---|---|---|---|
| 4,189,426 | 2/1980 | Li | 260/112.5 |
| 4,342,832 | 8/1982 | Goeddel et al. | 435/172 |
| 4,446,235 | 5/1984 | Seeburg | 435/91 |
| 4,621,053 | 11/1986 | Sugimoto | 435/68 |
| 4,755,465 | 7/1988 | Gray et al. | 435/70 |
| 4,769,361 | 9/1988 | Burleigh et al. | 514/12 |
| 4,791,099 | 12/1988 | Aroonsakul | 514/2 |
| 4,816,439 | 3/1989 | Jorgensen | 514/12 |
| 4,833,166 | 5/1989 | Grosvenor et al. | 514/12 |
| 4,837,202 | 6/1989 | Edwards, III et al. | 514/12 |
| 4,859,600 | 8/1989 | Gray et al. | 435/252.33 |
| 4,863,901 | 9/1989 | Wilmore | 514/12 |
| 4,898,830 | 2/1990 | Goeddel et al. | 435/320 |
| 4,939,124 | 7/1990 | Cacabelos | 514/12 |

OTHER PUBLICATIONS

Hoyt, D., et al., "Head Injury: An Immunologic Deficit in T-cell Activation", *The Journal of Trauma*, vol. 30, No. 7, (1990), pp. 759-767.

Cease, K. et al., "T-Cell Immunity and Vaccine Engineering-Application to the AIDS Virus," *AIDS Vaccine Research and Clinical Trials*, (1990), pp. 139-156.

Orloff, G. et al., "Interaction of HIV With Its Cellular Receptor, CD4", *AIDS Vaccine Research and Clinical Trials*, (1990), pp. 63-92.

Niall, H., "Revised Primary Structure for Human Growth Hormone", *Nature New Biology*, vol. 230, Mar. 17, 1971, pp. 90-91.

Chawla, R., et al., "Structural Variants of Human Growth Hormone: Biochemical, Genetic, and Clinical Aspects", *Ann. Rev. Med.*, vol. 34, 1983, pp. 519-547.

Isaksson, O., et al., "Mode of Action of Pituitary Growth Hormone on Target Cells", *Ann. Rev. Physiol.*, 1985, vol. 47, pp. 483-499.

Thorner, M., et al., "Growth Hormone, 1988", *J. Clin. Invest.*, vol. 82, (1988), pp. 745-747.

Hughes, J. et al., "The Nature and Regulation of the Receptors for Pituitary Growth Hormone", *Ann. Rev. Physiol.*, vol. 47, (1985), pp. 469-482.

Moore, J. et al., "Equiv. Potency & Pharmacokinetics of Recombinant HGH's . . . ", *Endocrinology*, vol. 122, (1988), pp. 2920-2926.

Baroni, "Thymus, Peripheral Lymphoid Tissues and Imm. Resp. of the Pituitary Dwarf Mouse", *Experientia*, vol. 23, (1967), pp. 281-283.

Pierpaoli, W. et al., "Relationship Between Thymus and Hypophysis", *Nature*, vol. 215, Aug. 19, (1967), pp. 834-837.

Marsh, J., et al., "Enhanced Growth & Immune Development in Dwarf Chicken . . . " *Proc. Soc. Exp. Biol. Med.*, vol. 175, (1984), pp. 351-360.

Fabris, N., et al., "Hormones and the Immunological Capacity", *Clin. Exp. Immunol.*, vol. 9, (1971), pp. 209-225.

(List continued on next page.)

Primary Examiner—Michael G. Wityshyn
Assistant Examiner—Choon Park Koh

[57] ABSTRACT

A method for stimulating the immune system by treating an individual who has been immunocompromised as a result of severe trauma, including closed head injury and infection, with human growth hormone. This treatment leads to an increase in total lymphocyte number, and in an increase in the T4/T8 ratio. The treatment represents an effective therapy for maintaining or stimulating the immunocompetence of an individual who has been immunocompromised.

27 Claims, 1 Drawing Sheet

OTHER PUBLICATIONS

Goff, B., et al., "Growth Hormone Treatment Stimulates Thymulin Production in Aged Dogs", *Clin. Exp. Immunol.*, vol. 68, (1987), pp. 580–587.

Franco, P., et al., "Influence of Growth Hormone on the Immunosuppressive Effect of Prednisolone in Mice", *Acta Endocrinologica (Copenhn)*, vol. 123, (1990), pp. 339–344.

Boutin, Jean-Marie, et al., "Identification of a cDNA Encoding a Long Form of Prolactin. . .," *Molecular Endocrinol.*, vol. 9, (1989), pp. 1455–1461.

Leung, D. et al., "Growth Hormone Receptor and Serum Binding Protein: Purification, Cloning and Expression", *Nature*, vol. 330, No. 6148, (1987), pp. 537–543.

Freemark, M. et al., "A Unique Placental Lactogen Receptor: Implications for Fetal Growth", *Endocrinology*, vol. 120, No. 5, (1987), pp. 1865–1872.

Millard, W., et al., "Growth Hormone and Thyrotropin Secretory Profiles and Provocative Testing in Aged Rats", *Neurobiology of Aging*, vol. 11, (1990), pp. 229–235.

Takahashi, S. et al., "Growth Hormone Secretory Patterns in Young, Middle-Aged and Old Female Rats", *Neuroendocrinology*, vol. 46, 1987, pp. 137–142.

Rudman, D. et al., "Impaired Growth Hormone Secretion in the Adult Population", *J. Clin. Invest.*, vol. 67, 1981, pp. 1361–1369.

Rudman, D. et al., "Effects of Human Growth Hormone in Men Over 60 Years Old", *The New England Journal of Medicine*, vol. 323, No. 1, 1990, pp. 1–6.

Vance, M. L., "Growth Hormone for the Elderly", *The New England Journal of Medicine*, 1990, pp. 52–54.

Nicoll, C. et al., "Structural Features of Prolactins and Growth Hormones . . . ", *Endocrine Reviews*, vol. 7, No. 2, (1988), pp. 169–203.

Chang, Chung Nan, et al, "High-level Secretion of Human Growth Hormone by *Escherichia coli*", *Gene*, vol. 55, 1987, pp. 189–196.

Rapaport, R., et al., "Suppression of Immune Function in Growth Hormone-Deficient Children. . . ", *The J. of Pediatrics*, vol. 109, (1986), pp. 434–439.

Murphy, W. et al., "*The FASEB Journal*", 75th Annual Meeting, Abstracts-Part III, Atlanta, Ga., vol. 5, No. 6, Apr. 21–25, (1991), A1669.

Durum, S. et al., *The FASEB Journal*, 75th Annual Meeting, Abstracts, Part III, Atlanta Ga., vol. 5, No. 6, Apr. 21–25, (1991), A1674.

Kelley, K., "Growth Hormone in Immunobiology", *Psychoneuroimmunology*, 2nd Edition, Robert Ader et al. (eds), Academic Press, N.Y., pp. 377–402.

Ammann, A., "Growth Hormone and Immunity," *Human Growth Hormone, Progress and Challenges*, Marcel Dekker, Inc., N.Y., L. E. Underwood (ed).

Weigent D., et al., "Growth Hormone and the Immune System", *Progress in NeuroEndocrinImmunology*, vol. 3, No. 4, (1990), pp. 231–241.

Kelley, K., "Growth Hormone, Lymphocytes and Macrophages", *Biochemical Pharmacology*, vol. 38, No. 5 (1989), pp. 705–713.

Rapaport, R., et al., "Effects of Human Growth Hormone on Immune Functions . . . ", *Life Sciences*, vol. 41, No. 20, (1987), pp. 2319–2324.

Bozzola, M. et al., "Immunological and Endocrinological Response to Growth Hormone Therapy in Short Children", *Acta Paediatr Scand.*, vol. 77, (1988), pp. 675–680.

Verland, S. et al. "Functional Receptors for Insulin-like Growth Factors I and II . . . ", *Molecular and Cellular Endocrinology*, vol. 67, (1989), pp. 207–216.

Pandian, M. et al., "Effect of Growth Hormone on the Metabolism of Thymus . . . ", *J. of Exper. Med.*, vol. 134, (1971), pp. 1095–1113.

Pierpaoli, W. et al., "Hormones and Immunologic Capacity", vol. 101, No. 6, (1968), pp. 1036–1043.

Gupta, et al., "Immunological Studies in Patients With Isolated Growth Hormone Deficiency", *Clin. Exp. Immunol.*, vol. 54, (1983), pp. 87–90.

Roth, J. et al., "Improvement in Clinical Condition and Thymus Murphologic . . . ", *Am. J. Vet Res.*, vol. 45, No. 6, (1984), pp. 1151–1155.

Goeddel, D., "Direct Expression in *Escherichia coli* of DNA Sequence. . .", *Nature*, vol. 281, (1979), pp. 544–548.

Gray, G. et al., "Periplasmic Production of Correctly Processed Human . . . ", *Gene*, vol. 39, (1985), pp. 247–254.

Kiess, W. et al., "Lymphocyte Subset Distribution and Natural Killer . . . ", *Clin Immunol. and Immunopathology*, vol. 48, (1988), pp. 85–94.

Cryer, H., "Immunologic Dysfunction Following (List continued on next page.)

OTHER PUBLICATIONS

Trauma", *Advances in Trauma and Critical Care*, vol. 6, Mosby Yearbook, (1991), pp. 53–71.

Behrman, S. "The Effect of Growth Hormone on Nutritional Markers . . . ", *Surgical Forum*, (1990), pp. 21–23.

"Growth and Neuroendocrine Dysfunction in Children with Acquired Immunodeficiency Syndrome", *The Journal of Pediatrics*, Oct. 1990, pp. 541–545.

"Effects of Hormones on Development and Function of Lymphoid Tissues", *Immunology*, 1969, pp. 303–314.

"Thymic Hormone Containing Cells. II. Evolution of Cells Containing the Serum Thymic Factor (FTS or Thymulin) in Normal and Autoimmune Mice, as Revealed by Anti-FTS Monoclonal Antibodies. Relationship with Ia Bearing Cells", *Clin. Exp. Immunol.*, 1983, pp. 1–6, W.

"Growth Hormone Mediates the Growth of T-Lymphoblast Cell Lines Via Locally Generated Insulin-Like Growth Factor-I", *Journal of Clinical Endocrinology and Metabolism*, 1990, vol. 71, No. 2, pp. 464–469.

"Tissue Distribution of Insulin-Like Growth Factor I and II Messenger Ribonucleic Acid in the Adult Rat", *Endocrinology*, 1987, vol. 120, No. 4, pp. 1279–1282.

"Alveolar Macrophages Release an Insulin-Like Growth Factor I-Type Molecule", *The Journal of Clinical Investigation, Inc.*, vol. 82, Nov. 1988, pp. 1685–1693.

"Insulin-Like Growth Factor Secretion by Human B-Lymphocytes: A Comparison of Cells from Normal and Pygmy Subjects"; *Journal of Clinical Endocrinology and Metabolism*, 1989, vol. 69, No. 5, pp. 978–984.

"Insulin-Like Growth Factor I Stimulates Erythropoiesis in Hypophysectomized Rats"; *Proc. Natl. Acad. Sci.*, Oct. 1988, vol. 35, pp. 7825–7829.

"Enhancement of Human Granulopoiesis in Vitro by Biosynthetic Insulin-Like Growth Factor I/Somatomedin C and Human Growth Hormone"; *The Journal of Clinical Investigation, Inc.*, vol. 81, Mar. 1988, pp. 791–797.

"Effect of Purified Somatomedins on Thymidine Incorporation into Lectin-Activated Human Lymphocytes", *Endocrinologica*, 1983, vol. 102, pp. 21–26.

"Insulin-Like Growth Factor-I Binds Selectively to Human Peripheral Blood Monocytes and B-Lymphocytes", *Journal of Clinical Endocrinology and Metabolism*, 1991, vol. 72, No. 5, pp. 1117–1122.

"A Novel Role of Growth Hormone and Insulin-Like Growth Factor-I", *The Journal of Immunology*, 1991, vol. 146, No. 5, pp. 1602–1608.

"Structural and Functional Characterization of the Human T Lymphocyte Receptor for Insulin-Like Growth Factor I In Vitro", *The Journal of Clinical Investigation, Inc.*, Sep. 1988, vol. 82, pp. 950–957.

"Growth Hormone Basic and Clinical Aspects", Proceedings of the 1st Nordisk Insulin Symposium, Stockholm, Sweden, Jun. 29–Jul. 1, 1987.

"Recombinant Human Insulin-Like Growth Factor I Stimulates Growth and has Distinct Effects on Organ Size in Hypophysectomized Rats", *Proc. Natl. Acad. Sci.*, Jul. 1988, vol. 85, pp. 4889–4893.

"Repopulation of the Atrophied Thymus in Diabetic Rats by Insulin-Like Growth Factor I", *Proc. Natl. Acad. Sci.*, May 1990, vol. 87, pp. 3690–3694.

"Program and Abstracts", 73rd Annual Meeting, Jun. 19–22, 1991.

"Type I and II Insulin-Like Growth Factor Receptors on Human Phytohemagglutinin-Activated T Lymphocytes", *Cellular Immunology*, 1987, vol. 109, pp. 318–331.

"IGF Receptors on Activated T Cells", pp. 326–331.

"Further Characterization of the Role of Corticosterone in the Loss of Humoral Immunity in Zinc-Deficient A/J Mice as Determined by Adrenalectomy", *The Journal of Immunology*, 1980, vol. 124, No. 6, pp. 2650–2655.

"Augmentation des Taux Circulants de Thymuline au Cours de L'hyperprolactinemie et de L'acromegalie", *C. R. Acad. Sci.*, Paris t. 310, Series III, pp. 7–13 (1990).

"Potential Therapeutic Indications for Growth Hormone and Growth Hormone-Releasing Hormone in Conditions Other Than Growth Retardation", *Pharmacotherapy*, Dec. 1986, vol. 6, No. 6, pp. 311–318.

Figure 1. The effect of placebo and HGH at 0.2 mg/kg on T4 levels.
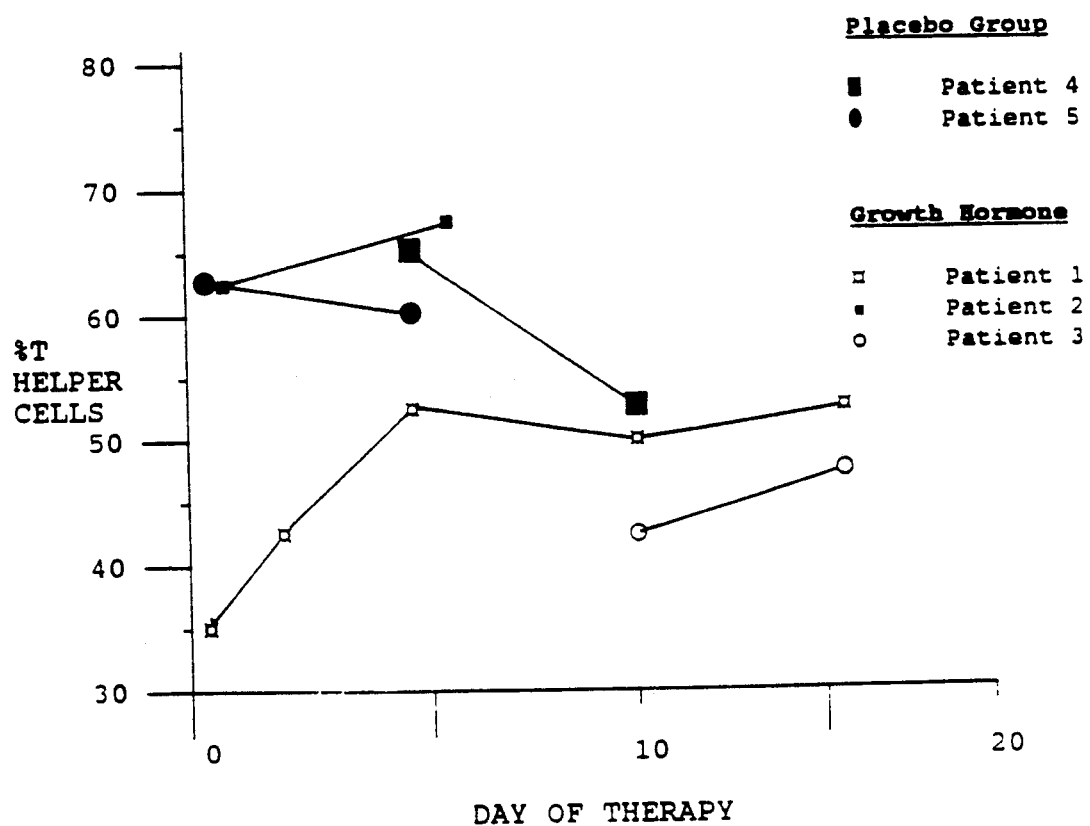

HUMAN GROWTH HORMONE INDUCED IMPROVEMENT IN DEPRESSED T4/T8 RATIO

This application is a continuation of application Ser. No. 07/770,919, filed Oct. 4, 1991 now abandoned.

BACKGROUND OF THE INVENTION

1. Field of the Invention

This invention relates to a method for stimulating the cells of the immune system of a human by administering human growth hormone. More particularly, the invention relates to a method for increasing the total lymphocyte count of a human by administering human growth hormone. Even more particularly, the invention relates to a method for increasing the T4/T8 ratio in a human by administering human growth hormone.

2. Background Art

The immune systems of vertebrates generally provide a dual mechanism for recognizing and eliminating materials which are foreign to the body. These mechanisms, which are ordinarily referred to as humoral (antibody mediated) and cellular immunity, are provided by B- and T- lymphocytes, respectively.

The immune response to foreign material, or antigens, involves complex interactions of various lymphocytes, or B-and T-cells. These interactions can be severely compromised following certain infections and after injury. T-cells, which are derived from the thymus, are particularly important for the maintenance of immunocompetence following injury (Hoyt, et al., *J. of Trauma*, Vol. 30, p. 759, 1990).

There are several subsets of T-cells which are named by their functions. Helper T-cells ($T_H$) are involved in the activation of B-cells into plasma cells which produce antibodies, which in turn, react with foreign antigens. $T_H$ cells express a surface antigen called CD4 or T4. T4+ cells comprise predominantly $T_H$ cells, along with another type of T-cell, called the accessory T-cell ($T_A$). Cytotoxic T-cells ($T_C$) are involved in the destruction of antigen-bearing cells. Another cell, derived from the same precursor as the T-cell, the natural killer (NK) cell, aids the $T_C$ in protecting the body from tumor cells. $T_C$ cells express a different surface antigen from $T_H$ cells which is called CD8 or T8. T8+ cells consist of T-cells with both suppressor ($T_S$) and cytotoxic activities. T-cell function and a normal T4/ T8 ratio are important to providing cellular immunity, which, in particular, defends the body from foreign antigens including invaders such as bacteria, fungi, parasites, and viruses.

The ratio of T4+ to T8+ cells is tightly regulated in humans, and has recently been shown to decrease as a result of severe head injury (See e.g. Hoyt, et al, 1990). This decreased T4/T8 ratio may result from alterations in the production of various cytokines, alterations to macrophages and their metabolites, and by activation of $T_S$ cells which inhibit the proliferation of other T-cells. Activation of $T_S$ cells probably may occur as a result of injury-induced serum suppressor substances such as prostaglandin $E_2$ (PGE$_2$), leukotrienes, tumor necrosis factor, and lymphocyte and proteolytic fragments of cytokines and their receptors.

A decreased T4/T8 ratio has also been shown to be characteristic of patients having acquired immune deficiency syndrome (AIDS) which is caused by infection with human immunodeficiency virus (HIV; Cease, et al., in *AIDS Vaccine Research and Clinical Trials*, Putney and Bolognesi, eds., p. 139, 1990). In the case of AIDS, one mechanism for the decreased T4/T8 ratio is the utilization of the T4 molecule by HIV as a cellular receptor. In binding to the T4 molecule, the virus is provided entry to that particular cell, which ultimately results in disablement of the normal cellular functions. The decrease in circulating T4+ lymphocytes is caused not only by the death of these cells following infection, but also from the loss of cell surface expression of T4 molecules on HIV infected T4+ cells (Orloff and McDougal, in *AIDS Vaccine Research and Clinical Trials*, Putney and Bolognesi, eds., p. 63, 1990). Infection by other viruses, which do not use the T4 molecule as a receptor, may result in immune suppression by other mechanisms which are not all completely understood. Oncogenic or tumor forming viruses can cause immunosuppression by inducing cells to form tumors which release immunosuppressive factors. Other viruses, such as cytomegalovirus (CMV) and lactic dehydrogenase virus (LDV) inhibit cellular and humoral immunity by unknown mechanisms.

HGH is a 191 amino acid single chain protein which is released by the anterior pituitary. It has a molecular weight of 21,500 kilodaltons and has disulfide bonds linking amino acids 53 and 165 and amino acids 182 and 189 (Niall, *Nature New Biol.* Vol. 230, p. 90, 1977). HGH is a potent anabolic agent, especially due to retention of nitrogen, phosphorus, potassium and calcium.

HGH causes a variety of physiological and metabolic effects in various animal models including linear bone growth, lactation, activation of macrophages, insulin-like and diabetogenic effects (Chawla, et al., *Ann. Rev. Med.* Vol. 34, p. 519, 1983; Isaksson, et al., *Ann. Rev. Physiol.*, Vol. 47, p. 483, 1985; Edwards, et al. *Science* Vol. 239, p. 769, 1988; Thorner and Vance, *J. Clin. Invest.* Vol. 82, p. 745, 1988; Hughes and Friesen, *Ann. Rev. Physiol.* Vol. 47, p. 469, 1985). Treatment of hypophysectomized rats with GH can restore at least a portion of the growth rate of the rats (Moore, et al., *Endocrinology*, Vol. 122, p. 2920, 1988).

A connection has been said to exist between the anterior pituitary and the immune system, and specifically with GH. Human growth hormone (HGH) is believed to be necessary for maintaining lymphoid tissues populated with lymphocytes. In mice, GH removal results in thymic atrophy, which can be reversed by readministration of GH (Baroni, *Experientia*, Vol. 23, p. 282, 1967). Two groups of investigators concluded from their studies that GH controls the growth of lymphoid tissue (Pierpaoli and Sorkin, *Nature*, Vol. 215, p. 834, 1967; Baroni, *Experientia*, Vol. 23, (1967). Subsequently, immunologic function was restored in the pituitary dwarf mouse by a combination of bovine somatotropic hormone and thyroxin (Baroni et al., *Immunol.*, Vol. 17, p. 303, 1969).

In a sex-linked dwarf chicken strain, bovine GH treatment resulted in enhanced antibody responses and bursal growth while thyroxine treatment stimulated thymus growth (Marsh et al., *Proc. Soc. Exp. Biol. Med.*, Vol. 175, p. 351, 1984). However, neither treatment altered immune function in the autosomal dwarf chicken. Bovine GH therapy alone partially restored immunologic function in immunodeficient Weimaraner dogs (Roth et al., *Ann. J. Vet. Res.*, Vol. 45, p. 1151, 1984).

Mice with hereditary GH deficiency develop an impairment of the immune system associated with thymic atrophy, immunodeficiency, and wasting, resulting in a shortened life expectancy (Frabris et al., *Clin. Exp. Immunol.*, Vol 9, p. 209, 1971). It has been shown that an age-associated decline in the plasma concentration of thymulin (a thymic hormone) occurs and that plasma thymulin concentration increases in bGH-treated middle-aged and old dogs (Goff et al., *Clin. Exp. Immunol.*, Vol 68, p. 580, 1987). Further, administration of HGH to $C_{57}/B1/6J$ mice was found to reverse the inhibitory effect of prednisolone on thymus and spleen cellularity and on natural killer activity; administration of HGH without prednisolone had no effect, although at higher doses it induced a decrease of thymic parameters and natural killer activity with no effect on spleen cellularity, and relative weights (Franco et al., *Acta Endocrinologica*, Vol. 123, p. 339, 1990).

Two different human receptors have been cloned with which HGH appears to interact; the HGH liver receptor (Leung et al., *Nature*, Vol. 330, p. 537, 1987) and the human prolactin receptor (Boutin et al., *Mol. Endocrinol.* Vol. 3, p. 1455, (1989). However, there may be others including the human placental lactogen receptor (Freemark, et al., *Endocrinol.* Vol. 120, p. 1865, 1987). These homologous receptors contain a glycosylated extracellular hormone binding domain, a single transmembrane domain and a cytoplasmic domain which differs considerably in sequence and size. One or more receptors play a role in determining the physiological response to HGH.

It has been reported that, especially in women after menopause, GH secretion declines with age. Millard et al., *Neurobiol, Aging*, Vol. 11, p. 229, 1990; Takahashi et al., *Neuroendocrinology*, Vol. 46, p. 137, 1987). See also Rudman et al., *J. Clin. Invest.*, Vol. 67, p. 1361, 1981 and Blackman, *Endocrinology and Aging*, Vol. 16, p. 981, 1987. Moreover, a report exists that some of the manifestations of aging, including decreased lean body mass, expansion of adipose-tissue mass, and the thinning of the skin, may be reduced by GH treatment three times a week. See, e.g., Rudman et al., *N. Eng. J. Med.*, Vol. 323, p. 1, 1990 and the accompanying article in the same journal issue by Dr. Vance (pp. 52–54).

HGH is released in response to stimulation by human growth hormone releasing hormone, hGHRH, which is released by the hypothalamus. hGHRH is also referred to as human growth hormone releasing factor, hGHRF or GRF, as somatoliberin or as somatocrinin. HGH stimulates the growth of many tissues of the body, exerting many of its effects by stimulating the secretion of other growth factors, such as the somatomedins, which display insulin-like activities (U.S. Pat. No. 4,769,361). A major biological effect of HGH is to promote growth in young mammals and to maintain tissues in older mammals. The organ systems affected include the skeleton, connective tissue, muscles, and viscera such as liver, intestine, and kidneys. Growth hormone exerts its effect through interaction with specific receptors on the target cell's membrane. HGH is a member of a family of homologous hormones that include placental lactogens, prolactins, and other genetic and species variants of growth hormone (Nicoll, et al., *Endocrine Reviews*, Vol. 7, p. 169, 1986). HGH is unusual among these in that it exhibits broad species specificity and binds to either the cloned somatogenic (Leung, et al. *Nature*, Vol. 330, p. 537, 1987) or prolactin receptor (Boutin, et al., *Cell*, Vol. 53, p. 69, 1988). The cloned gene for HGH has been expressed in secreted form in *E. coli* (Chang, et al. (11987) *Gene*, Vol. 39, p. 247, 1987). The effects of HGH include linear growth (somatogenesis), lactation, activation of macrophages, and other insulin-like and diabetogenic effects (Chawla, *Ann. Rev. Med.*, Vol. 34, p. 519, 1983; Edwards, et al., *Science*, Vol. 239, p. 769, 1988; Thorner, et al., *J. Clin. Invest.*, Vol. 81, p. 745, 1988).

HGH has been used primarily in the treatment of hypopituitary dwarfism (Rapaport, et al., *J. of Pediatrics*, Volume 109, p. 434, 1986). HGH treatment in growth hormone deficient patients results in the stimulation of skeletal growth, an increase in cellular protein synthesis, an increase in serum glucose and insulin levels, a reduction in body fat stores, and stimulation of connective tissue and mineral metabolism. Among its most striking effects in hypopituitary (GH-deficient) subjects is accelerated linear bone growth of bone-growth-plate-cartilage resulting in increased stature (Kaplan, *Growth Disorders in Children and Adolescents*, Springfield, Ill., Charles C. Thomas, 1964).

In addition to being used to stimulate growth, HGH has also been used as a dietary supplement to maintain a positive nitrogen balance (U.S. Pat. No. 4,863,901), for the treatment of intoxicated individuals (U.S. Pat. No. 4,816,439) and for the treatment and diagnosis of neurodegenerative diseases such as Alzheimer's Disease and Parkinson's Disease (U.S. Pat. Nos. 4,939,124 and 4,791,099). Growth hormone (obtained from either rats or pigs) has also been shown to act on the immune system of animals by increasing the production of macrophages, and by activating their oxidative metabolism (U.S. Pat. No. 4,837,202).

Studies have also recently been conducted on GH and T-cell proliferation in the thymus (Murphy et al., *FASEB Meeting Abstract*, Atlanta, April 1991; Durum et al., *FASEB Meeting Abstract*, Atlanta, April 1991). For other articles on the immune effects of GH, see Kelley, "Growth Hormone in Immunobiology," in *Psychoneuroimmunology II*, 2nd Ed., B. Ader et al., eds., Acad. Press 1990, and Ammann, "Growth Hormone and Immunity," in *Human Growth Hormone--Progress and Challenges*, L. Underwood, ed., Marcel Dekker, Inc., New York, p. 243, 1988; and Weigent and Blalock, *Prog. NeuroEndocrinImmunology*, Vol 3, p. 231, 1990; and Kelly, *Biochem. Pharmacol.*, Vol. 38, p. 705, 1989.

Human growth hormone treatment has been shown to suppress some immunological functions in growth hormone-deficient children (Rapaport, et al., 1986, Bozzola, et al., *Acta. Paediatr. Scand.*, Vol. 74, p. 675, 1988). However, there is a difference in the responses of lymphocytes from growth hormone-deficient patients and normal controls to HGH. Rapaport et al. reported that when HGH was administered to normal subjects, a significant depression in spontaneous lymphocyte proliferation was seen. In contrast, a significant increase in proliferation was demonstrated when HGH was administered to the growth hormone deficient group. (Rapaport, et al., *Life Sciences*, Vol. 41, p. 231, 1987). It therefore appears that HGH has different effects on immune function, depending on the status of the patient's hormonal interactions and baseline immune responsiveness. Some studies suggest that administration of HGH to HGH deficient patients decreases the T4/T8 ratio (Rapaport, et al., 1986).

SUMMARY OF THE INVENTION

It has now been found that the T4/T8 ratio in an individual with a depressed T4/T8 ratio is increased with administration of HGH. Thus the present invention provides a therapy for patients with conditions that result in depressed T4/T8 ratios. Specifically, the present invention provides a method for increasing the T4/T8 ratio in a human with a depressed T4/T8 ratio by the administration of an amount of human growth hormone effective to increase the ratio to a level normal for said human.

BRIEF DESCRIPTION OF THE DRAWINGS

FIG. 1 illustrates the effect of placebo and HGH at 0.2 mg/kg on T4 levels.

DETAILED DESCRIPTION OF THE PREFERRED EMBODIMENTS OF THE INVENTION

The present invention provides a method for treating an individual with human growth hormone to restore immunocompetence to patients who have an immunologic deficit. More particularly, the present invention provides a method for increasing the T4/T8 ratio in a human with a depressed such ratio by administering an amount of HGH effective to increase that ratio. Even more particularly, the present invention provides a method for increasing the T4/T8 ratio in a non-growth hormone deficient human with a depressed such ratio by administering an amount of HGH effective to increase that ratio. By returning a person's T4/T8 ratio to a normal level or above a normal level, there is an improved immune response to complicating infections which occur after the depression in the T4/T8 ratio occurs. Improving the T4/T8 ratio may also decrease the potential for a patient to develop malignancies which arise as a result of a lowered T4/T8 ratio. Such malignancies include Kaposi's Sarcoma, which is a common malignancy which develops in AIDS patients and lymphoma which frequently occurs in transplant patients.

T4/T8 ratios are tightly regulated by the immune system, and generally fall in the range of 1 to 4 in normal humans, with a mean of 2.5. The importance of the regulation of the T4/T8 ratio lies in the different functions of T4 versus T8 cells. The function of the cells which make up the T4 population is to aid other immune cells in their functions. $T_H$ cells interact with mature B cells to promote antibody production, while $T_A$ cells secrete growth factors that aid in $T_C$ cell development and cellular immunity. Thus T4+ cells may be considered positive regulators of the immune system. T8+ cells on the other hand, $T_C$ and $T_S$ cells, function to kill cells expressing foreign antigens and to suppress immune responses, respectively. Thus the T8+ cells may be considered as negative regulators of the immune response. It is believed therefore, that the ratio of T4+ cells to T8+ cells correlates with the level of activation of the immune system. An inverted ratio, or a ratio of less than one indicates a low level of immune responsiveness. Therefore, while increasing the absolute number of all T cells may not lead to a more activated immune system, because the activator and suppressor activities may cancel the effect of the other, increasing the T4/T8 ratio would lead to an increased activation of the immune system.

The ratio of the T4+ to T8+ cells is indicative of the level of activation of the immune system, because T4+ cells aid in the function of other immune cells, while certain T8+ cells suppress the function of other immune cells. Physical trauma, such as injury and infection, can result in T4/T8 ratios which are abnormally low. Any decrease in the T4/T8 level below baseline for that individual is considered pathologic; however, a ratio which is inverted, (i.e. less than 1) is considered to be highly pathologic. Closed head injury is one trauma which has been shown to result in a T4/T8 ratio below baseline for that individual. There are several possible mechanisms for this reduction, including the activation of suppressor T-cells, disrupted synthesis and release of various cytokines, and the release of certain suppressor substances.

The present invention demonstrates that administration of above 0.1 mg/kg/day of HGH has been shown to return abnormally low T4/T8 ratios to a normal level. In addition, HGH treatment of patients with closed head injury has been shown to result in increased total lymphocyte number.

The immunological deficit treatable with HGH results from a variety of causes, including stress, disease, tissue transplant, infection and physical trauma. The magnitude of injury of certain trauma patients, such as those suffering from multiple blunt trauma, can be defined by the Injury Severity Score (ISS) and the index of the number of injuries and the severity of injuries that the body has sustained. Patients suffering from penetrating trauma can be evaluated with the ISS or the Abdominal Trauma Index (ATI). The therapy of the present invention is useful for treating those who do not have a HGH deficit as well as those who do have a HGH deficit.

Infections which result in depressed T4/T8 ratios and which may be treated by the present invention include viral infections from viruses such as cytomegalovirus (CMV), lactic dehydrogenase virus (LDV), oncogenic DNA viruses, oncogenic RNA viruses such as human T-lymphotropic viruses I and II (HTLV-I, HTLV-II), non-oncogenic retroviruses such as HIV, and any other virus which causes a decrease in the T4/T8 ratio. Other infections which may be treatable by the present invention are those which cause a decrease in the T4/T8 ratio. These diseases include viral, bacterial and fungal infections. Malignancies may also compromise the immune system and that effect on the immune system may be susceptible to treatment with the present invention.

The deficit in the T4/T8 ratio can be manifested in a number of ways, including decreased cell number, decreased proliferative response, decreased expression of cellular activation markers and immunoregulatory lymphokines, decreased microbial killing due to oxidative deficits in superoxide and peroxide, and the like.

Human growth hormone useful in practicing the present invention can be obtained from any source known to produce substantially pure HGH. Years ago, HGH was purified from the pituitaries of cadavers for use in the treatment of dwarfism. Presently, in addition to being isolated from the pituitary gland, HGH can be isolated from hybridoma lymphoblastoid cell lines and can be synthesized chemically or on an automated peptide synthesizer. With the advent of recombinant DNA technology, HGH can now also be produced in vitro in large enough quantities to satisfy the demand (U.S. Pat. Nos. 4,446,235, 4,342,832, 4,755,465, 4,859,600 and 4,898,830). The disclosure of each of the foregoing patents is incorporated herein by reference. For the present invention, HGH is preferably obtained using recombinant DNA sources which are transformed into prokaryotic or eukaryotic cells in vitro. These prokaryotic cells include bacteria such as $E.$ $coli$ and Pseudomonas and the eukaryotic cells include cells such as yeast and mammalian tissue culture cells.

Fragments of HGH which retain the biological activity of HGH may also be used in the present invention. One such fragment is HGH which lacks the NH$_2$-terminal methionine.

As an alternative to direct administration of HGH, human growth hormone releasing hormone or factor (hGHRH or hGRF) may be used to cause stimulation of the release of HGH from the pituitary, and therefore to effect an increase in the T4/T8 ratio. Also, fragments of hGHRH may be used which are known to retain the releasing hormone activity of hGHRH. These fragments may include fragments containing amino acids 1-27 or 1-29.

HGH can be administered by any method known in the art, including injection, controlled release implants, or genetic therapy whereby the HGH gene is delivered into cells, or administered using a viral vector, such as a retrovirus. More preferably, the HGH is administered by injection, preferably intramuscularly. hGHRH is preferably administered intravenously or subcutaneously.

For parenteral administration, in one embodiment, the HGH is formulated generally by mixing it at the desired degree of purity, in a unit dosage injectable form (solution, suspension, or emulsion), with a pharmaceutically acceptable carrier, i.e. one that is non-toxic to recipients at the dosages and concentrations employed and is compatible with other ingredients of the formulation. For example, the formulation preferably does not include oxidizing agents and other compounds that are known to be deleterious to polypeptides.

The HGH formulation used in the present invention can contain HGH as the only active ingredient, or it can contain other active ingredients such as pharmaceutical compositions, hormones or growth factors. One example of a growth factor which may be used in combination with HGH is insulin-like growth factor 1 (IGF-1). Any combination of ingredients may be used which either potentiates or does not diminish the therapeutic effects of HGH on the T4/T8 ratio.

Generally, the formulations are prepared by contacting the HGH uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid and other organic acids or their salts; antioxidants such as ascorbic acid; low molecular weight (less that about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The GH is typically formulated in such vehicles at a concentration of about 0.1 mg/ml to 100 mg/ml, preferably 1-10 mg/ml, at a pH of about 3 to 8. GH is generally stable at a pH of 6.5 to 8, more preferably 7.2 to 7.8. GH used for therapeutic administration must be sterile. Sterility is readily accomplished by filtration through sterile filtration membranes (e.g. 0.2 micron membranes). GH ordinarily will be stored in unit or multi-unit dose containers, for example, sealed ampules or vials, as an aqueous solution or as a lyophilized formulation for reconstitution.

HGH can be administered at any concentration that effects a positive response by the immune system. When administered by intramuscular injection, the dosage is preferably 0.1 mg/kg to 0.5 mg/kg, and more preferably about 0.2 mg/kg. In general, however, effective dosages may be about 0.2 mg/kg and higher with the upper limit determined by the ability of the patient to safely absorb the HGH. Effective dosages of hGHRH and its fragments are in the range of 1-10 $\mu$g/kg of body weight administered intravenously, or 5-50 $\mu$g/kg of body weight administered subcutaneously. This dosage can be administered every 6, 12 or 24 hours.

HGH can be administered at any time after the event which causes the immunocompromised condition, but earlier therapy is beneficial because it may avoid the $T_S$ cell domination aspect of the immunosuppression. Therapy is preferably begun within two weeks of the event. HGH can be administered for an extended period of time, but positive effects on the immune system can be measured within two weeks of the initial administration, and generally at five to 7 days. Ratios achieved with HGH can exceed about 7:1.

T4/T8 ratios should be continually monitored to determine whether further therapy is needed. There is no known upper limit for the ratio of T4/T8 cells, however, the goal of therapy is a ratio between 1 and 10, and more preferably between 1 and 5. It may in some instances, however, be therapeutic to treat individual with HGH to attain a higher ratio, above 10, and perhaps also about 15 or higher for a short period of time. There is no known detriment to temporarily maintaining a ratio this high.

The patient's T4/T8 ratio must be monitored to determine the length of therapy required. Some patients may only require the initial therapy to boost their immune response. Other patients, with more chronic symptoms such as those caused by tissue transplants or AIDS, may require continuous therapy with maintenance dosages of HGH.

In order to evaluate the initial levels of T4 and T8 populations of cells, to determine required dosages of HGH to increase these levels, and to determine the levels of these cells after treatment, the T-cell populations must be isolated from the blood, their cellular metabolisms investigated and their cell surface molecules identified. The cells must then also be quantitated. Dosage can be optimized by monitoring the change in T4+ and T8+ cell numbers as dosage is increased.

Measurement of the effects on the immune system can be obtained by methods known in the art, including measurement of lymphokine protein and RNA levels, measurement of oxidative metabolism, measurement of cellular activation marker levels, measurement of cell number, examination of the proliferative response of the cells in response to antigenic or mitogenic stimuli, and the like. Preferably, the cells are labelled with antibodies to cell markers and cells are counted on a fluorescence activated cell sorter (FACS) or flow cytometer. Labelling of the cells with the antibodies can also yield information on the level of cellular activation markers.

Characterization of the different cell populations by identification of the cells' surface markers include any antibodies known in the art which will identify the cells as immune cells. These antibodies can be polyclonal or monoclonal in nature, but are preferably monoclonal. Important cell surface markers, or cell surface cluster of differentiation markers (CD) include T11 or CD2, which identifies all T cells, T4 or CD4, which identifies T helper (and accessory) cells, I3 which identifies activated T cells, T8 or CD8, which identifies cytotoxic and suppressor T cells, T3 which identifies mature circulating T cells and T cells in the thymic medulla, and NKH-1 or CD56, which identifies natural killer cells.

Cells can be labelled so that they may be identified using a flow cytometer or FACS, by labelling with a fluorescent or dye-conjugated antibody. The primary or anti-cell differentiation marker antibody may be directly labelled, or indirect immunofluorescence may be used where a labelled secondary is allowed to bind to the primary antibody. The secondary antibody is made in a species other than the species used to generate the primary antibody, and is made to specifically bind to immunoglobulins from the species which generated the primary antibody. Any marker known in the art can be used which will serve to identify the cell, including fluorescein isothiocyanate (FITC), rhodamine, phycoerythrin red and the like.

Cells can be isolated from the subject using any method known in the art. Preferably, blood is isolated from the subject into a tube containing an anti-coagulant. Antibodies to the cell surface molecules can be adsorbed on the cells using any method known in the art. Preferably, the cells contained in the isolated blood and anticoagulant are added to a solution of the antibody for the surface marker to be tested.

Lymphocytes can be prepared using any method known in the art, such as selective affinities to substrates, density gradients and the like. More preferably, an erythrocyte lysing system, such as the Q-prep leukocyte preparation system is used. This system is a three component reagent system which consists of an erythrocyte lysing agent, a leukocyte stabilizer and a preservative. The reagents are added and the tube is centrifuged. Approximately half the volume in the tube can be aspirated off leaving a high concentration of labelled cells, which can then be analyzed.

The following examples are presented in order to more fully illustrate the preferred embodiments of the invention. They should in no way be construed, however, as limiting the broad scope of the invention.

EXAMPLE 1

Within eight days of injury, 14 consecutive, nonseptic adult patients with severe closed head injury who required enteral nutritional support were randomized to receive placebo, which consisted of just the pharmaceutical carrier without HGH (n=5), or recombinant HGH at a concentration of 0.(n=5) or 0.2 (n=4) mg/kg (Nutropin ® brand HGH from Genentech, Inc.) in a pharmaceutical carrier by intramuscular injection for 10 days. Patients were administered a mean protein dose of 1.8 g/kg/d and a mean nonprotein calorie dose of 31.6 kcal/kg/d. Peripheral whole blood was collected by venipuncture in a vacuum tube containing sodium heparinate. 2 μl of T11 antibody, conjugated to FITC and obtained from Coulter Clone was pipetted into an empty 12×75 mm test tube. 100 μl of the anticoagulated whole blood was added to the antibodies and incubated for 10 minutes at room temperature. The Q-prep (Coulter Clone) leukocyte preparation system was used to prepare leukocytes. Reagents A, B and C were added sequentially and the tubes then centrifuged on a Hermle Z 260k centrifuge for two minutes at 2200 rpm. One half the volume in each test tube was aspirated off, leaving a high concentration of approximately 100 μl labelled leukocytes. The cells were measure using an EPICS Profile II Flow Cytometer.

Table 1 illustrates the effect of recombinant HGH on the total lymphocyte count of nonseptic trauma patients.

TABLE 1

Effect of recombinant HGH on nonseptic trauma patients.

| | Study Groups | | |
|---|---|---|---|
| | Placebo | 0.1 mg/kg HGH | 0.2 mg/kg HGH |
| Total lymphocyte count, No./mm³ | 1,811 ± 439 | 1,440 ± 444 | 2,620 ± 1,693 |

All values represent mean ±5.0 on day 10 except where noted. HGH indicates human growth hormone.
P < 0.05 compared to placebo.
P < 0.05 from baseline within group.

EXAMPLE 2

Five patients with closed head injury were used in this study. Three patients received HGH in a pharmaceutical carrier at 0.2 mg/kg, and two patients in the placebo group received just the pharmaceutical carrier without HGH. 2 μl of the appropriate amount of each monoclonal antibody (T4, T8 or T11 antibody, conjugated to FITC and obtained from Coulter Clone) was used to label cells. Blood was isolated and cells were labelled as in Example 1. The results of this study are illustrated in FIG. 1.

Table 2 illustrates the effect of placebo and HGH at 0.2 mg/kg on T4 and T8 subpopulations. Table 3 indicates the percentage increases in the T4/T8 ratios of patients for whom there is a Day 0 value.

TABLE 2

The effect of placebo and HGH at 0.2 mg/kg on T4 and T8 subpopulations.

| Patient | Group | Day | T4 | T8 | T4/T8 |
|---|---|---|---|---|---|
| 1 | HGH | 0 | 36.5 | 22.2 | 1.64 |
| | | Post | 53.9 | 28.2 | 1.91 |
| 2 | HGH | 0 | 61.7 | 16.4 | 3.76 |
| | | 7 | 65.2 | 8.6 | 7.58 |
| 3 | HGH | 10 | 42.5 | 24.0 | 1.77 |
| | | Post | 46.8 | 22.0 | 2.13 |
| 4 | Placebo | 5 | 61.6 | 10.9 | 5.65 |
| | | 10 | 52.2 | 21.4 | 2.44 |
| 5 | Placebo | 0 | 61.1 | 14.8 | 4.12 |
| | | 5 | 60.0 | 20.2 | 3.00 |

TABLE 3

Percentage increases in patients' T4/T8 ratios.

| Patient | Group | % Increase in T4/T8 |
|---|---|---|
| Patient 1 | HGH | 16.5% |
| Patient 2 | HGH | 101.6% |

TABLE 3-continued

Percentage increases in patients' T4/T8 ratios.

| Patient | Group | % Increase in T4/T8 |
|---|---|---|
| Patient 5 | Placebo | −27.2% |

While the invention has been described and illustrated herein by references to various specific materials, procedures and examples it is understood that the invention is not restricted to the particular material combinations of material, and procedures selected for that purpose. Numerous variations of such details can be implied as will be appreciated by those skilled in the art.

What is claimed is:

1. A method for increasing the T4/T8 ratio in a human with a depressed T4/T8 ratio comprising administering an amount of human growth hormone effective to increase the ratio to a level normal for said human.

2. A method according to claim 1, wherein the human growth hormone is recombinantly produced.

3. A method according to claim 1, wherein said depressed ratio is below baseline for said human.

4. A method according to claim 1, wherein said depressed ratio is inverted.

5. A method according to claim 2, wherein the amount of human growth hormone administered is from above 0.mg to 0.5 mg of HGH per kg of said human's weight per day.

6. A method according to claim 5, wherein administration of human growth hormone increases the T4/T8 ratio to a level between 1 and 10.

7. A method according to claim 6, wherein administration of human growth hormone increases the T4/T8 ratio to a level between 2 and 5.

8. A method for increasing the T4/T8 ratio in a human with a depressed T4/T8 ratio comprising administering an amount of human growth hormone effective to increase the ratio to a level normal for said human wherein said depressed T4/T8 ratio results from a physical trauma.

9. A method according to claim 8, wherein the human growth hormone is recombinantly produced.

10. A method according to claim 8, wherein said depressed ratio is below baseline for said human.

11. A method according to claim 8, wherein said depressed ratio is inverted.

12. A method according to claim 9, wherein the amount of human growth hormone administered is from above 0.1 mg to 0.5 mg of HGH per kg of said human's weight per day.

13. A method according to claim 12, wherein administration of human growth hormone increases the T4/T8 ratio to a level between 1 and 10.

14. A method according to claim 13, wherein administration of human growth hormone increases the T4/T8 ratio to a level between about 2 and 5.

15. A method according to claim 9, wherein the trauma is a closed head injury.

16. A method for increasing the T4/T8 ratio in a human with a depressed T4/T8 ratio comprising administering an amount of human growth hormone effective to increase the ratio to a level normal for said human wherein said depressed T4/T8 ratio results from an infection.

17. A method according to claim 16, wherein the human growth hormone is recombinantly produced.

18. A method according to claim 16, wherein said depressed ratio is below baseline for said human.

19. A method according to claim 16, wherein said depressed ratio is inverted.

20. A method according to claim 17, wherein the amount of human growth hormone administered is from above 0.1 mg to 0.5 mg of HGH/kg of said human's weight per day.

21. A method according to claim 20, wherein administration of human growth hormone increases the T4/T8 ratio to a level between 1 and 10.

22. A method according to claim 21, wherein administration of human growth hormone increases the T4/T8 ratio to a level between 2 and 5.

23. A method according to claim 17, wherein the infection is a viral infection.

24. A method according to claim 23, wherein the virus causing the infection is human immunodeficiency virus.

25. A method according to claim 17, wherein the infection is a bacterial infection.

26. A method for increasing the T4/T8 ratio in a human with a depressed T4/T8 ratio comprising administering human growth hormone releasing hormone or a fragment thereof to said human in an amount sufficient to cause the release of an amount of human growth hormone effective to increase the ratio to a level normal for said human.

27. A method according to claim 26, wherein the amount of human growth hormone releasing hormone or biologically active fragment thereof administered is from 1–200 μg/kg of said human's weight per day.

* * * * *